(12) United States Patent
Blette

(10) Patent No.: US 9,546,281 B1
(45) Date of Patent: *Jan. 17, 2017

(54) TATTOO STENCIL COMPOSITION AND METHOD FOR MANUFACTURING

(71) Applicant: RandD Enterprises of San Jose, LLC, Hastings, MN (US)

(72) Inventor: Russell E. Blette, Hastings, MN (US)

(73) Assignee: RANDD ENTERPRISES OF SAN JOSE, LLC, Hastings, MN (US)

(*) Notice: Subject to any disclaimer, the term of this patent is extended or adjusted under 35 U.S.C. 154(b) by 236 days.

This patent is subject to a terminal disclaimer.

(21) Appl. No.: 14/304,128

(22) Filed: Jun. 13, 2014

Related U.S. Application Data

(63) Continuation of application No. 13/204,661, filed on Aug. 6, 2011, now Pat. No. 8,784,553.

(60) Provisional application No. 61/371,719, filed on Aug. 8, 2010.

(51) Int. Cl.
| | |
|---|---|
| *C09D 5/00* | (2006.01) |
| *A61M 37/00* | (2006.01) |
| *B41M 1/12* | (2006.01) |
| *C09D 191/00* | (2006.01) |
| *B41M 1/30* | (2006.01) |
| *A61Q 1/02* | (2006.01) |

(52) U.S. Cl.
CPC .......... *C09D 5/008* (2013.01); *A61M 37/0076* (2013.01); *A61Q 1/025* (2013.01); *B41M 1/12* (2013.01); *B41M 1/30* (2013.01); *C09D 191/00* (2013.01)

(58) Field of Classification Search
CPC ..... A61Q 1/025; A61M 37/0076; B41M 1/12; B41M 1/30; C09D 5/008; C09D 191/00
See application file for complete search history.

(56) References Cited

U.S. PATENT DOCUMENTS

| | | | |
|---|---|---|---|
| 2,857,315 A | 10/1958 | Teller | |
| 4,504,465 A | 3/1985 | Sampson et al. | |
| 5,275,496 A | 1/1994 | Fattori et al. | |
| 5,407,668 A | 4/1995 | Kellner | |
| 6,881,253 B2 | 4/2005 | Dhuey | |
| 8,784,553 B2 * | 7/2014 | Blette | C09D 11/0235 106/243 |
| 2004/0221401 A1 | 11/2004 | Desenne et al. | |

* cited by examiner

*Primary Examiner* — David M Brunsman
(74) *Attorney, Agent, or Firm* — DuFault Law Firm, P.C.; Dustin R. DuFault

(57) ABSTRACT

The present invention is a tattoo stencil chemical composition comprising stearic acid, triethanolamine, a humectant to retain moisture on a user's skin, water and a preservative chemical composition that includes 56% propylene glycol, 30% diazolidinyl urea, 11% methylparaben and 3% propylparaben. The tattoo stencil chemical composition can also be sterilized by gamma rays or ethylene oxide and injected into a flexible wipe, one or more packets or a bulk hands free dispenser. The invention also includes a method for manufacturing a tattoo stencil chemical composition.

17 Claims, 2 Drawing Sheets

TATTOO STENCIL COMPOSITION AND METHOD FOR MANUFACTURING

CROSS REFERENCE TO RELATED APPLICATIONS

This application claims priority to similarly entitled U.S. Non-Provisional application Ser. No. 13/204,661, filed Aug. 6, 2011, now U.S. Pat. No. 8,784,883, which claimed the benefit of now expired U.S. Provisional 61/371,719 filed on Aug. 8, 2010, the disclosures of which are each incorporated herein in their entirety by reference.

TECHNICAL FIELD & BACKGROUND

The tattooing process starts with a selection of artwork by the customer. Customers may choose from art on display that has already been drawn, or may have an artist create a new piece of artwork. The tattoo artist produces an outline of the artwork, which is then transferred to the skin using image transfer paper and a transfer fluid and is then utilized as a reference for a transdermal ink application.

Two types of image transfer paper are generally utilized. Hectograph paper can be utilized with a pressure method to transfer a desired tattoo outline from a sheet of plain paper onto the transfer paper. Suitable pressure transfer methods include hand tracing or the utilization of a dot matrix printer. Thermal paper can be utilized for hand tracing or a thermal copier can be utilized to transfer an outline from a sheet of regular paper onto the transfer paper.

Both types of transfer paper, hectograph and thermal, are then transferred to the skin by using a formulation based on an active chemical composition found in SPEED STICK™ deodorant. Using either transfer method, once the design has been attached to the transfer sheet, the design is cut from the transfer sheet, resulting in a produced stencil that is then applied to the customer's skin. First, the customer's skin is cleaned and shaved. The skin is moistened with a transfer lotion to allow the tattoo dye to adhere to the person's skin. A glycerin-based solution containing the chemical composition sodium stearate (such as contained in SPEED-STICK™ deodorant, for example) is especially suitable. Then the stencil is pressed onto the skin, with the dye contacting the moistened skin. The transfer sheet is then carefully removed, leaving the dye and tattoo design on the skin.

Because the resulting reference design lies on the skin's surface, the dye and the transfer lotion that are applied are pushed into the skin during the tattooing process. However, the transfer lotions traditionally utilized are not specially formulated for use on human skin and are typically not sterilized, thereby possibly leading to infection or other health concerns.

It is an object of the present invention to provide a tattoo stencil composition that transfers a tattoo stencil relatively easily, quickly and accurately that also remains a relatively long time on a person's skin.

It is an object of the present invention to provide a tattoo stencil composition that is packaged in individual packets or in a hands-free dispenser for sterilization and sanitary purposes.

It is an object of the present invention to provide a tattoo stencil composition and a method for manufacturing a tattoo stencil composition to apply a tattoo.

What is really needed is a tattoo stencil composition that transfers a tattoo stencil relatively easily, quickly and accurately that also remains a relatively long time on a person's skin that is packaged in individual packets or in a hands-free dispenser for sterilization and sanitary purposes and a method for manufacturing a tattoo stencil composition to apply a tattoo.

BRIEF DESCRIPTION OF THE DRAWINGS

The present invention will be described by way of exemplary embodiments, but not limitations, illustrated in the accompanying drawing in which like references denote similar elements, and in which.

DETAILED DESCRIPTION OF ILLUSTRATIVE EMBODIMENTS

Figure 1A:
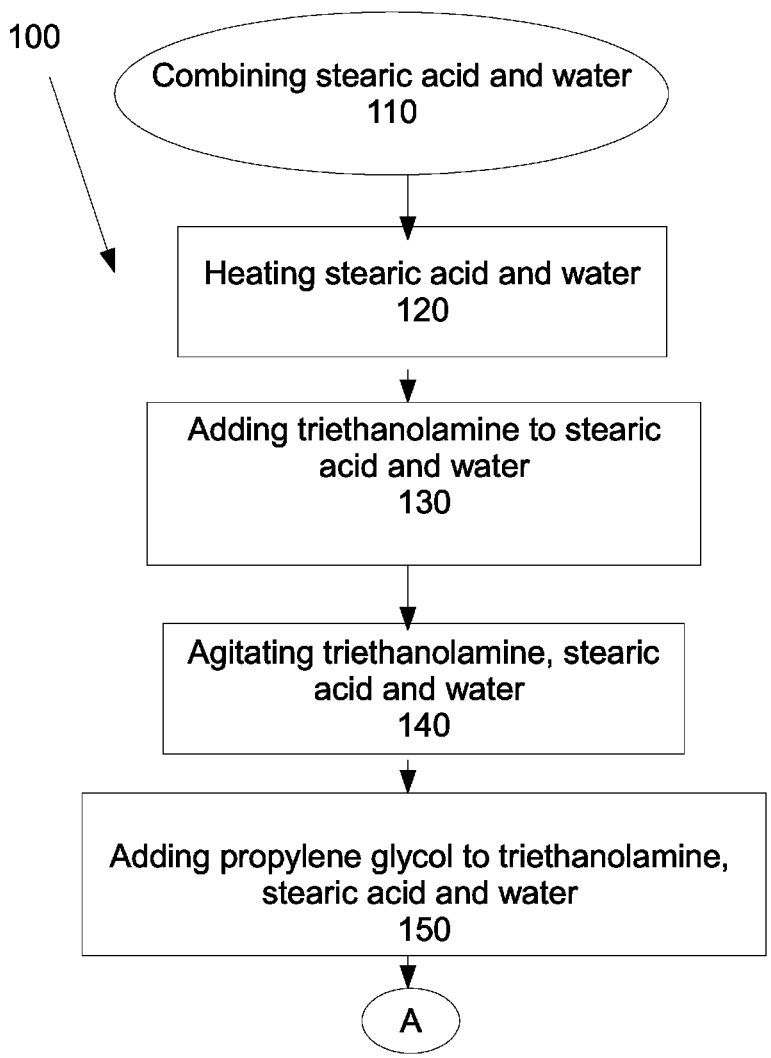
FIGS. 1A and 1B illustrate a method for manufacturing a tattoo stencil composition, in accordance with one embodiment of the present invention.

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

The present invention includes a tattoo stencil composition and method for using the tattoo stencil composition. The tattoo stencil composition is a stencil transfer liquid for the transfer of tattoo stencils easily, quickly and accurately, that lasts and stays a relatively long time on a person's skin that is having a tattoo applied with the tattoo stencil composition.

In one embodiment, the tattoo stencil composition can be packaged in individual packets or in a hands free dispenser.

In one embodiment, the tattoo stencil composition is sterilized by gamma rays or an ethylene oxide composition. The treated tattoo stencil composition can then also be injected into a flexible wipe as well.

Example 1

The tattoo stencil chemical composition (in parts by weight) includes:
- 0.5 parts by weight stearic acid;
- 10.1 parts by weight water;
- 0.27 parts by weight triethanolamine;
- 2.9 parts by weight propylene glycol; and
- 0.01 parts by weight preservative chemical composition that includes 56% propylene glycol, 30% diazolidinyl urea, 11% methylparaben and 3% propylparaben.

The 0.5 parts by weight stearic acid can be substituted with a suitable fatty acid. The 10.1 parts by weight water is one selected from the group consisting of 10.1 parts by weight of distilled water, de-ionized water or tap water or any combination of 10.1 parts by weight distilled water, de-ionized water and tap water. The 0.27 parts by weight triethanolamine can be substituted with any other suitable compound with an amino group. The 2.9 parts by weight propylene glycol serves as a humectant to retain moisture on a user's skin. The 2.9 parts by weight propylene glycol can be substituted with glycol or glycerin. The preservative chemical composition that includes 56% propylene glycol, 30% diazolidinyl urea, 11% methylparaben and 3% propylparaben is also known commercially as Germaben II, although other suitable types of preservative chemical compositions can also be utilized with the tattoo stencil chemical composition.

The tattoo stencil chemical composition includes stearic acid that is in the ranges of approximately 0.0001% by weight to 9% by weight of the tattoo stencil chemical composition, approximately 1% by weight to 6% by weight of the tattoo stencil chemical composition and approximately 2% by weight to 3% by weight of the tattoo stencil chemical composition. The stearic acid is an aqueous acid form and other suitable aqueous acids may also be utilized with the tattoo stencil chemical composition.

The tattoo stencil chemical composition includes triethanolamine that is in the range of approximately 0.0001% by weight to 3% by weight of the tattoo stencil chemical composition, in the range of approximately 0.001% by weight to 2% by weight of the tattoo stencil chemical composition, in the range of approximately 0.01% by weight to 1% by weight of the tattoo stencil chemical composition and in the range of approximately 0.027% by weight to 0.5% by weight of the tattoo stencil chemical composition. The triethanolamine is a PH balancer that helps control the PH or acidity of the tattoo stencil chemical composition, which will be relatively high due to the stearic acid or aqueous acid in the tattoo stencil chemical composition. Other suitable PH balancers may also be utilized with the tattoo stencil chemical composition that can also include other suitable types of amines to substitute for the triethanolamine.

The tattoo stencil chemical composition includes a humectant which is propylene glycol, although other suitable humectants can be utilized in the tattoo stencil chemical composition. Any suitable quantity of propylene glycol or suitable humectants can be utilized by the tattoo stencil chemical composition.

The tattoo stencil chemical composition includes a solvent that is water that is in the range of approximately 0.0001% by weight to 99% by weight of the tattoo stencil chemical composition, in the range of approximately 1% by weight to 80% by weight of the tattoo stencil chemical composition and in the range of approximately 3% by weight to 70% by weight of the tattoo stencil chemical composition. Other suitable solvents may also be utilized with the tattoo stencil chemical composition.

The tattoo stencil chemical composition includes a preservative chemical composition that includes 56% propylene glycol, 30% diazolidinyl urea, 11% methylparaben and 3% propylparaben, which is commercially known as Germaben II. The preservative chemical composition is in the range of approximately 0.0001% by weight to 99% by weight of the tattoo stencil chemical composition, in the range of approximately 0.001% by weight to 88% by weight of the tattoo stencil chemical composition and in the range of approximately 0.01% by weight to 1% by weight of the tattoo stencil chemical composition. Other suitable preservative chemical compositions can also be utilized with the tattoo stencil chemical composition.

The tattoo stencil chemical composition can also include a viscosity-modifying agent that can be any type of viscosity-modifying agent. The tattoo stencil chemical composition can also be sterilized by gamma rays. The sterilized tattoo stencil chemical composition can then be injected into a flexible wipe, one or more individual packets or a bulk hands free dispenser. Likewise, the tattoo stencil chemical composition can also be sterilized by ethylene oxide. The ethylene oxide treated tattoo stencil chemical composition can be injected into a flexible wipe, one or more individual packets or a bulk hands free dispenser.

The tattoo stencil chemical composition relates to methods and articles of manufacture such as stencil transfer liquids, for the transfer of tattoo stencils easily, quickly and accurately, that last and stay a relatively long time on the skin. Additionally, the transfer liquid can be packaged in individual packets or in a hands free dispenser. Further, the articles of manufacture may be sterilized for hygienic use on human skin.

In one embodiment, the stencil transfer formulation is sterilized by gamma rays or EO (Ethylene oxide). It is then injected into a flexible wipe or bulk hands free dispenser.

After the outline stencil is transferred to the customer's skin, the lines are used as a reference for the tattoo artist as he applies the tattoo ink while continuously checking the full-color drawing as the tattoo artist works to copy the details of the graphic. The formulations of the tattoo stencil chemical composition allow for the creation of a longer lasting stencil transfer onto the skin. This allows for more accurate and efficient work by the tattoo artist. The products and methods of the tattoo stencil chemical composition also extend the time period before the need to reapply the stencil during the tattooing process because the stencil has washed off.

Figure 1B:
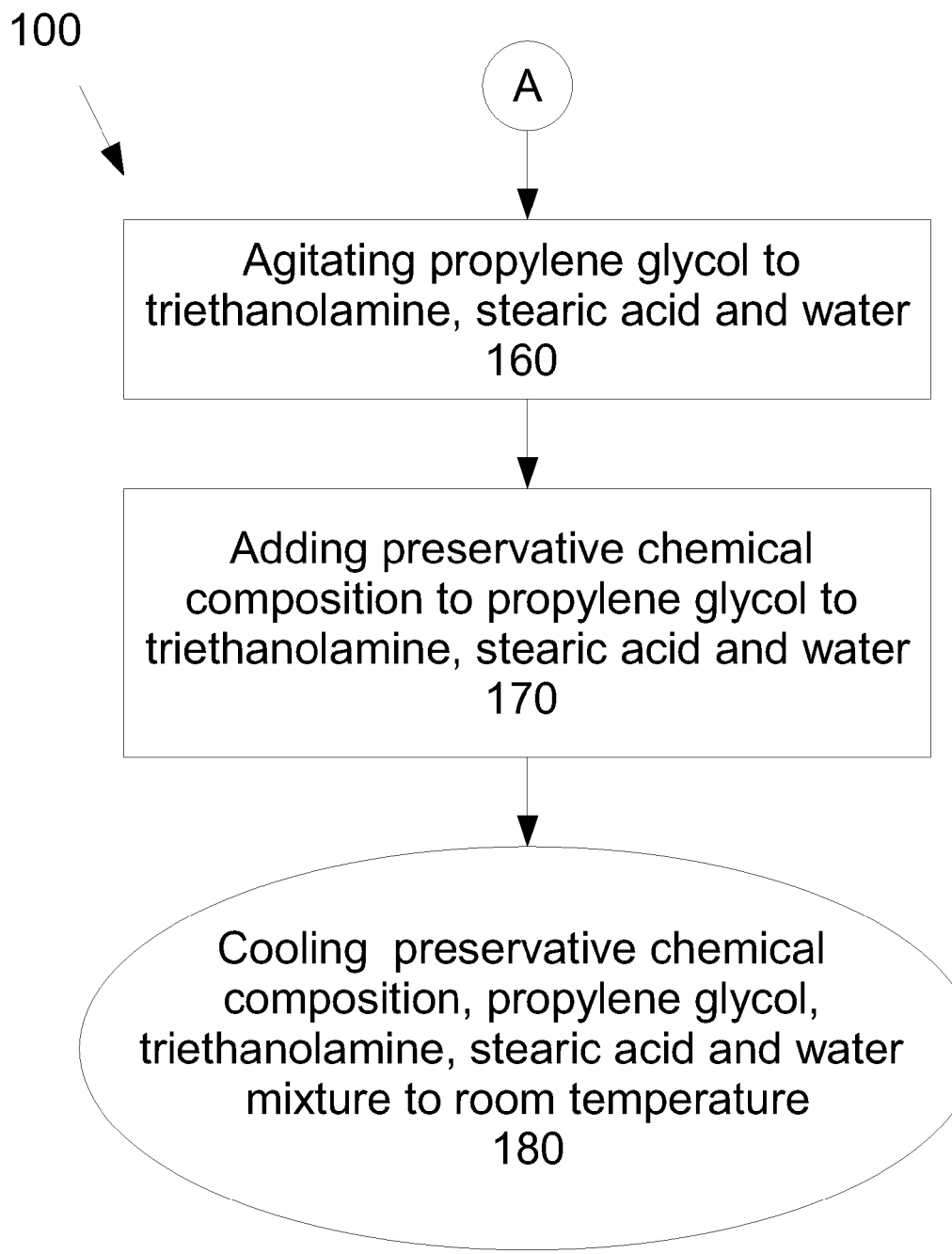

FIGS. 1A and 1B illustrate a method 100 for manufacturing a tattoo stencil composition, in accordance with one embodiment of the present invention. The method 100 includes the steps of combining stearic acid and 110, heating the combined stearic acid and water 120, adding a quantity of triethanolamine to the heated combined stearic acid and water 130, agitating the combined stearic acid, water and triethanolamine mixture 140, adding a quantity propylene glycol or other glycol or glycerin to the agitated stearic acid, water and triethanolamine 150, agitating the agitated stearic acid, water, triethanolamine and added propylene glycol or other glycol or glycerin, adding preservative chemical composition that includes propylene glycol, diazolidinyl urea, methylparaben and propylparaben to said agitated stearic acid, water, triethanolamine and added propylene glycol or other glycol or glycerin 170 and cooling the mixture of stearic acid, water, triethanolamine, added propylene glycol or other glycol or glycerin and includes approximately propylene glycol, diazolidinyl urea, methylparaben and propylparaben to room temperature 180.

A method for manufacturing a tattoo stencil composition includes combining 0.5 parts by weight stearic acid and 10.1 parts by weight water and heating the combined stearic acid and water in the range of 110 F-140 F. A quantity of 0.27 parts by weight of triethanolamine is then added to the heated combined stearic acid and water. The combined stearic acid, water and triethanolamine mixture is then agitated in the range of 10-20 minutes. A quantity of 2.9 parts by weight propylene glycol or other glycol or glycerin is then added to the agitated stearic acid, water and triethanolamine. The agitated stearic acid, water, triethanolamine and added propylene glycol or other glycol or glycerin is then agitated for 15 Minutes. The 0.01 parts by weight of preservative chemical composition that includes 56% propylene glycol, 30% diazolidinyl urea, 11% methylparaben and 3% propylparaben, which is commercially known as Germaben II, is then added to the agitated stearic acid, water, triethanolamine and added propylene glycol or other glycol or glycerin. The mixture of the stearic acid, water, triethanolamine, added propylene glycol or other glycol or glycerin and Germaben II is then cooled to room temperature.

Although the present invention has been described with reference to various embodiments, persons skilled in the art will recognize that changes may be made in form and detail without departing from the spirit and scope of the invention.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

The invention claimed is:

1. A tattoo stencil chemical composition, comprising:
   0.5 part by weight fatty acid;
   10.1 parts by weight water;
   0.27 part by weight triethanolamine;
   2.9 parts by weight propylene glycol; and
   0.1 part by weight of a preservative chemical composition that includes 56% propylene glycol, 30% diazolidinyl urea, 11% methylparaben and 3% propylparaben.

2. A tattoo stencil chemical composition, comprising:
   0.0001% to 9% by weight fatty acid;
   0.0001% and 99% by weight water;
   0.0001% to 3% by weight triethanolamine; and
   0.0001% by weight to 99% of a preservative chemical composition.

3. The tattoo stencil chemical composition of claim 2 further comprising glycol.

4. The tattoo stencil chemical composition of claim 2 further comprising propylene glycol.

5. The tattoo stencil chemical composition of claim 2 wherein the fatty acid is between 1% and 6% by weight.

6. The tattoo stencil chemical composition of claim 5 wherein the fatty acid is between 2% and 3% by weight.

7. The tattoo stencil chemical composition of claim 2 wherein the water is between 1% and 80% by weight.

8. The tattoo stencil chemical composition of claim 7 wherein the water is between 3% and 70% by weight.

9. The tattoo stencil chemical composition of claim 7 wherein the triethanolamine is between 0.001% and 2% by weight.

10. The tattoo stencil chemical composition of claim 9 wherein the triethanolamine is between 0.01% and 1% by weight.

11. The tattoo stencil composition of claim 2 wherein the fatty acid is between 1% and 6% by weight, wherein the water is between 1% and 80% by weight, and wherein the triethanolamine is between 0.001% and 2% by weight.

12. The tattoo stencil composition of claim 11 wherein the fatty acid is 2% and 3% by weight, wherein the water is between 3% and 70% by weight, and wherein the triethanolamine is between 0.01% and 1% by weight.

13. The tattoo stencil composition of claim 2 wherein the preservative chemical composition includes 56% propylene glycol, 30% diazolidinyl urea, 11% methylparaben and 3% propylparaben.

14. A method for manufacturing a tattoo stencil composition, comprising:
   combining a fatty acid at approximately 0.0001% to 9% by weight of the tattoo stencil chemical composition and water at approximately 0.0001% and 99% by weight of the tattoo stencil chemical composition;
   heating said combined fatty acid and water;
   adding a quantity of triethanolamine to said heated combined fatty acid and water such that the triethanolamine is in the range of approximately 0.0001% to 9% by weight of the tattoo stencil chemical composition;
   agitating said combined fatty acid, water and triethanolamine mixture;
   adding a quantity of propylene glycol or other glycol or glycerin to said agitated fatty acid, water and triethanolamine;
   agitating said agitated fatty acid, water, triethanolamine and added propylene glycol;
   adding approximately 0.0001% and 99% by weight of the tattoo stencil composition a preservative chemical composition that includes 56% propylene glycol, 30% diazolidinyl urea, 11% methylparaben and 3% propylparaben to said agitated fatty acid, water, triethanolamine and added propylene glycol or other glycol or glycerin; and
   cooling said mixture of fatty acid, water, triethanolamine, added propylene glycol or other glycol or glycerin and includes approximately propylene glycol, diazolidinyl urea, methylparaben and propylparaben to room temperature.

15. The method according to claim 14, wherein said water is one selected from the group consisting of distilled water, de-ionized water, tap water and any combination of distilled water, de-ionized water and tap water.

16. The method according to claim 14, wherein the tattoo stencil chemical composition comprises:
   0.5 part by weight fatty acid;
   10.1 parts by weight water;
   0.27 part by weight triethanolamine;
   2.9 parts by weight propylene glycol; and
   0.1 part by weight of the preservative chemical composition.

17. The method according to claim 14, further comprising adding a viscosity-modifying agent.

* * * * *